(12) United States Patent
Naito et al.

(10) Patent No.: US 9,134,246 B2
(45) Date of Patent: Sep. 15, 2015

(54) LIGHT SOURCE ADJUSTMENT UNIT, OPTICAL MEASUREMENT DEVICE, SUBJECT INFORMATION OBTAINING SYSTEM, AND WAVELENGTH ADJUSTMENT PROGRAM

(71) Applicant: CANON KABUSHIKI KAISHA, Tokyo (JP)

(72) Inventors: Jumpei Naito, Kawasaki (JP); Kota Iwasaki, Atsugi (JP); Masafumi Kyogaku, Yokohama (JP); Yoichi Otsuka, Kawasaki (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 14/290,833

(22) Filed: May 29, 2014

(65) Prior Publication Data

US 2014/0353504 A1 Dec. 4, 2014

(30) Foreign Application Priority Data

May 31, 2013 (JP) ................................. 2013-115682
Mar. 28, 2014 (JP) ................................. 2014-069415

(51) Int. Cl.
*G01J 5/02* (2006.01)
*G01N 21/65* (2006.01)
*G01J 3/44* (2006.01)

(52) U.S. Cl.
CPC .. *G01N 21/65* (2013.01); *G01J 3/44* (2013.01)

(58) Field of Classification Search
CPC ..... H01S 3/005; H01S 3/1305; H01S 3/0078; H01S 3/06758; H01S 3/083; H01S 3/094003; H01S 3/094038; H01S 3/094096; H01S 3/0941; H01S 3/10092; H01S 3/1301; H01S 3/1392; H01S 3/1394; H01S 3/1398
See application file for complete search history.

(56) References Cited

U.S. PATENT DOCUMENTS

| | | | | | |
|---|---|---|---|---|---|
| 5,179,422 | A | * | 1/1993 | Peterson | 356/237.1 |
| 5,353,791 | A | * | 10/1994 | Tamura et al. | 600/310 |
| 6,370,169 | B1 | * | 4/2002 | Imajuku et al. | 372/32 |
| 2002/0117632 | A1 | * | 8/2002 | Hakamata et al. | 250/458.1 |
| 2002/0186454 | A1 | * | 12/2002 | Sakurai | 359/333 |

(Continued)

FOREIGN PATENT DOCUMENTS

| JP | 2011-180504 A | 9/2011 |
|---|---|---|
| WO | WO2010/140614 A1 | 12/2010 |

OTHER PUBLICATIONS

Saar, et al., "Video-Rate Molecular Imaging in Vivo with Stimulated Raman Scattering", Science, Dec. 3, 2010, vol. 330, pp. 1368-1370.

*Primary Examiner* — David J Makiya
*Assistant Examiner* — Taeho Jo
(74) *Attorney, Agent, or Firm* — Canon USA Inc. IP Division

(57) ABSTRACT

An optical measurement device includes a light source unit including a first laser light source configured to emit a laser beam having a first wavelength and a second laser light source configured to emit a laser beam having a second wavelength, a measurement wave number setting unit, and a light source adjustment unit configured to adjust at least one of the first wavelength and the second wavelength such that a difference between or a sum of a first wave number corresponding to the first wavelength and a second wave number corresponding to the second wavelength matches a measurement wave number set through the measurement wave number setting unit.

20 Claims, 13 Drawing Sheets

(56) References Cited

U.S. PATENT DOCUMENTS

| | | | |
|---|---|---|---|
| 2003/0227629 A1* | 12/2003 | Dobbs et al. | 356/437 |
| 2003/0234932 A1* | 12/2003 | Nicolaides et al. | 356/445 |
| 2006/0012785 A1* | 1/2006 | Funk et al. | 356/301 |
| 2006/0012871 A1* | 1/2006 | Funk et al. | 359/385 |
| 2006/0017920 A1* | 1/2006 | Tsuchiya et al. | 356/317 |
| 2006/0039423 A1* | 2/2006 | Tokuhisa et al. | 372/22 |
| 2007/0024860 A1* | 2/2007 | Tobiason et al. | 356/498 |
| 2008/0024788 A1* | 1/2008 | Shimizu et al. | 356/497 |
| 2009/0207416 A1* | 8/2009 | Xiangqian et al. | 356/477 |
| 2010/0104241 A1* | 4/2010 | Oikawa et al. | 385/16 |
| 2011/0134421 A1* | 6/2011 | Baldwin et al. | 356/301 |
| 2012/0051755 A1* | 3/2012 | Arahira | 398/158 |
| 2012/0287428 A1* | 11/2012 | Tamada | 356/301 |
| 2013/0194582 A1* | 8/2013 | Tokimitsu | 356/498 |
| 2013/0222785 A1* | 8/2013 | Sasaki | 356/4.09 |
| 2014/0064728 A1* | 3/2014 | Atlas | 398/65 |
| 2014/0293388 A1* | 10/2014 | Matsumoto et al. | 359/9 |
| 2015/0109622 A1* | 4/2015 | Ota | 356/479 |

\* cited by examiner

FIG. 4A
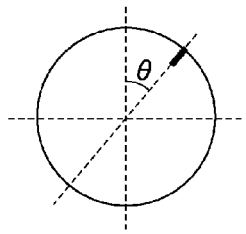
FIG. 4B
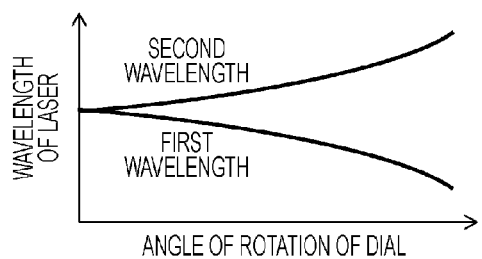
FIG. 4C
| ANGLE OF ROTATION OF DIAL [°] | WAVE NUMBER [cm⁻¹] | FIRST WAVELENGTH [nm] | SECOND WAVELENGTH [nm] |
|---|---|---|---|
| 0 | 0 | 1125 | 1125 |
| 10 | 56 | 1122 | 1128 |
| 20 | 111 | 1118 | 1132 |
| 30 | 167 | 1115 | 1135 |
| 90 | 500 | 1093 | 1157 |
| 180 | 1000 | 1061 | 1189 |
| 360 | 2000 | 1000 | 1250 |

| ANGLE OF ROTATION OF DIAL [°] | WAVE NUMBER [cm⁻¹] | FIRST WAVELENGTH [nm] | SECOND WAVELENGTH [nm] |
|---|---|---|---|
| 0 | 0 | 1050 | 1050 |
| 90 | $1.8 \times 10^3$ | 952 | 1148 |
| 180 | $3.6 \times 10^3$ | 855 | 1245 |
| 270 | $5.4 \times 10^3$ | 772 | 1318 |
| 360 | $7.2 \times 10^3$ | 700 | 1400 |

FIRST LASER LIGHT SOURCE 33

SECOND LASER LIGHT SOURCE 34

| ANGLE OF ROTATION OF DIAL [°] | WAVE NUMBER [cm⁻¹] | FIRST WAVELENGTH [nm] | SECOND WAVELENGTH [nm] |
|---|---|---|---|
| 0 | $3.6 \times 10^4$ | 200 | 700 |
| 30 | $4.0 \times 10^4$ | 182 | 700 |
| 90 | $4.9 \times 10^4$ | 158 | 700 |
| 180 | $6.2 \times 10^4$ | 133 | 700 |
| 345 | $8.6 \times 10^4$ | 100 → 200 | 700 → 800 |
| 360 | $8.8 \times 10^4$ | 100 | 800 |

FIG. 7A
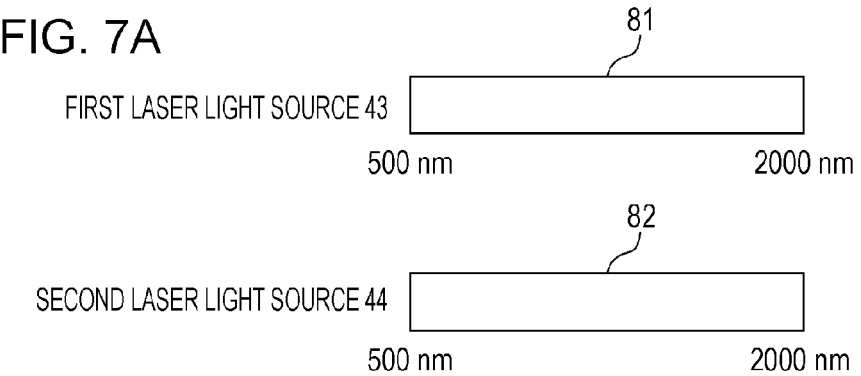
FIG. 7B
|   | WAVE NUMBER [cm⁻¹] | FIRST WAVELENGTH [nm] | SECOND WAVELENGTH [nm] |
|---|---|---|---|
| 1 | $7.13 \times 10^3$ | 500 | 777 |
| 2 | $7.13 \times 10^3$ | 700 | 1400 |
| 3 | $7.13 \times 10^3$ | 1000 | 3484 |
FIG. 7C
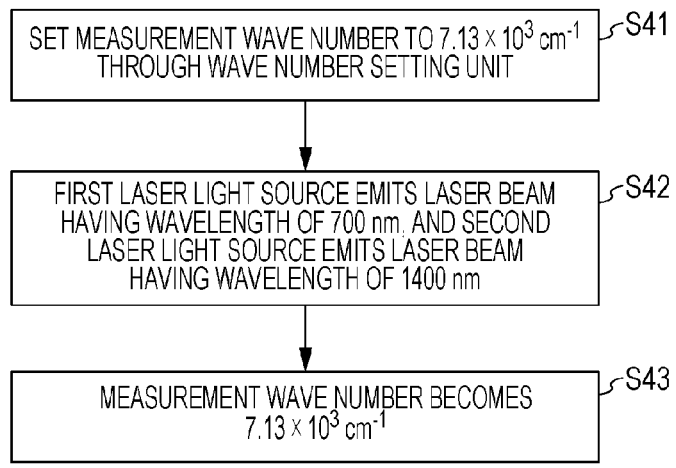

| ANGLE OF ROTATION OF DIAL [°] | MEASUREMENT WAVE NUMBER [cm⁻¹] | WAVE NUMBER OF FIRST LASER LIGHT SOURCE [cm⁻¹] | WAVE NUMBER OF SECOND LASER LIGHT SOURCE [cm⁻¹] |
|---|---|---|---|
| 0 | $1.0 \times 10^2$ | $4.0 \times 10^1$ | $6.0 \times 10^1$ |
| 45 | $5.5 \times 10^2$ | $2.4 \times 10^2$ | $3.1 \times 10^2$ |
| 90 | $1.0 \times 10^3$ | $4.0 \times 10^2$ | $6.0 \times 10^2$ |
| 180 | $1.9 \times 10^3$ | $8.0 \times 10^2$ | $1.1 \times 10^3$ |
| 360 | $3.7 \times 10^3$ | $1.5 \times 10^3$ | $2.2 \times 10^3$ |

FIG. 9A

| MEASUREMENT WAVE NUMBER [cm⁻¹] | FIRST WAVE NUMBER [cm⁻¹] | FIRST WAVELENGTH [nm] | SECOND WAVE NUMBER [cm⁻¹] | SECOND WAVELENGTH [nm] |
|---|---|---|---|---|
| $2.86 \times 10^4$ | $1.43 \times 10^4$ | 700 | — | — |
| $2.86 \times 10^4$ | $1.33 \times 10^4$ | 752 | $1.53 \times 10^4$ | 654 |

LIGHT SOURCE ADJUSTMENT UNIT, OPTICAL MEASUREMENT DEVICE, SUBJECT INFORMATION OBTAINING SYSTEM, AND WAVELENGTH ADJUSTMENT PROGRAM

BACKGROUND OF THE INVENTION

1. Field of the Invention

The present invention relates to optical measurement devices configured to carry out optical measurements by utilizing nonlinear optical phenomena; embodiments of the invention also relate to light source adjustment units and wavelength adjustment programs that are used in the optical measurement devices, and to subject information obtaining systems.

2. Description of the Related Art

In recent years, spectrometric devices that utilize nonlinear optical phenomena have been developed and used for observing small-sized organisms. Known spectroscopic techniques that utilize nonlinear optical phenomena include sum frequency generation spectroscopy and two-photon absorption spectroscopy. The use of such techniques makes it possible to observe unstained biological tissues.

In addition, optical measurement devices that utilize a phenomenon referred to as nonlinear Raman scattering, such as coherent anti-Stokes Raman scattering and stimulated Raman scattering, to obtain vibration information of molecules are being developed. In particular, optical measurement devices that utilize nonlinear Raman scattering phenomena (hereinafter, also referred to as nonlinear Raman scattering optical measurement devices) are expected to serve as devices for observing a substance distribution within a cell. It should be noted that, in the present invention and in the present specification, an optical measurement device corresponds to any device that carries out optical measurement, and examples of such a device include a device for measuring an optical spectrum and an optical microscope for carrying out optical observation.

In a nonlinear Raman scattering optical measurement device, a subject is irradiated with two laser beams having different wavelengths in such a manner that the laser beams form focuses within the subject. When a difference between the frequencies of the two laser beams coincides with the frequency of the molecular vibration of the molecules within the subject, the frequency of the molecular vibration of the molecules within the subject can be obtained by utilizing nonlinear Raman scattering phenomena in which scattering occurs specifically at the location(s) where the laser beams are focused. By detecting a change in the intensity of the scattered light while varying a difference between the frequencies of the incident laser beams, a Raman spectrum can be obtained. International Publication No. WO2010/140614 A1 and Brian G Saar et al., "Video-Rate Molecular Imaging in Vivo with Stimulated Raman Scattering", Science, vol. 330, No. 6009, 1368-1370 (2010) disclose techniques for obtaining a spatial distribution of a Raman spectrum at high speed while sweeping a wavelength at high speed in a stimulated Raman scattering optical measurement device.

Furthermore, sum frequency generation, difference frequency generation, two-photon fluorescence, two-photon absorption, multiphoton absorption, and other similar techniques are known as nonlinear optical phenomena where a dual-wavelength laser beam is used. In an optical measurement device that utilizes such phenomena, or in sum frequency generation spectroscopy, for example, a subject is irradiated with two laser beams having different frequencies and sum frequency light generated within the subject at that time is detected. This is effectively used for imaging cytoplasm or the like, while utilizing extremely high interface selectivity. In addition, while two-photon absorption spectroscopy utilizes a phenomenon in which two photons are absorbed simultaneously to shift to an excited state, in a case of dual-wavelength excitation in particular, light having a frequency that is equal to the sum of the frequencies of the incident two laser beams is detected. This allows light having a long wavelength to be used as incident light and is thus effectively used to observe, in particular, a relatively deep portion within an organism.

In optical measurement utilizing nonlinear optical phenomena, a spectrum is often expressed by using a wave number. As known by persons skilled in the art, the term "wave number" (also sometimes referred to as "wavenumber") is the reciprocal of the wavelength expressed in centimeters (cm), and represents a measure of the frequency of radiation. More generally, wavenumber=$1/\lambda$ is the measurement of the number of wavelengths per unit distance, where $\lambda$ is the wavelength. In the present invention and in the present specification, a wave number to be used for measurement in optical measurement utilizing nonlinear optical phenomena is referred to as a measurement wave number. In other words, in optical measurement utilizing nonlinear Raman scattering phenomena or difference frequency generation, a measurement wave number corresponds to a difference between the wave numbers of two laser beams with which a subject is irradiated. Meanwhile, in optical measurement utilizing sum frequency generation, two-photon absorption, or multiphoton absorption, a measurement wave number corresponds to a sum of the wave numbers of two or more laser beams with which a subject is irradiated.

SUMMARY OF THE INVENTION

According to an aspect of the present invention, an optical measurement device includes a light source unit including a first laser light source configured to emit a laser beam having a first wavelength and a second laser light source configured to emit a laser beam having a second wavelength, a measurement wave number setting unit, and a light source adjustment unit configured to adjust at least one of the first wavelength and the second wavelength such that a difference between or a sum of a first wave number corresponding to the first wavelength and a second wave number corresponding to the second wavelength matches a measurement wave number set through the measurement wave number setting unit.

Further features of the present invention will become apparent from the following description of exemplary embodiments with reference to the attached drawings.

BRIEF DESCRIPTION OF THE DRAWINGS

FIG. 4A illustrates an angle of rotation of a dial according to the first exemplary embodiment.

FIG. 4B is a graph schematically illustrating a relationship among the angle of rotation of the dial and the first and second wavelengths according to the first exemplary embodiment.

FIG. 4C is a table indicating a relationship among the angle of rotation of the dial, the measurement wave number, and the first and second wavelengths according to the first exemplary embodiment.

FIG. 7A schematically illustrates ranges within which the wavelengths of the first and second laser light sources can be set according to a fourth exemplary embodiment.

FIG. 7B illustrates combinations of the first and second wavelengths that can achieve a measurement wave number of $7.13 \times 10^3$ cm$^{-1}$.

FIG. 7C illustrates a flow of processes for setting and adjusting the measurement wave number according to the fourth exemplary embodiment.

FIG. 9A is a table indicating the measurement wave number, the first and second wavelengths, and the first and second wave numbers.

DESCRIPTION OF THE EMBODIMENTS

Figure 1:
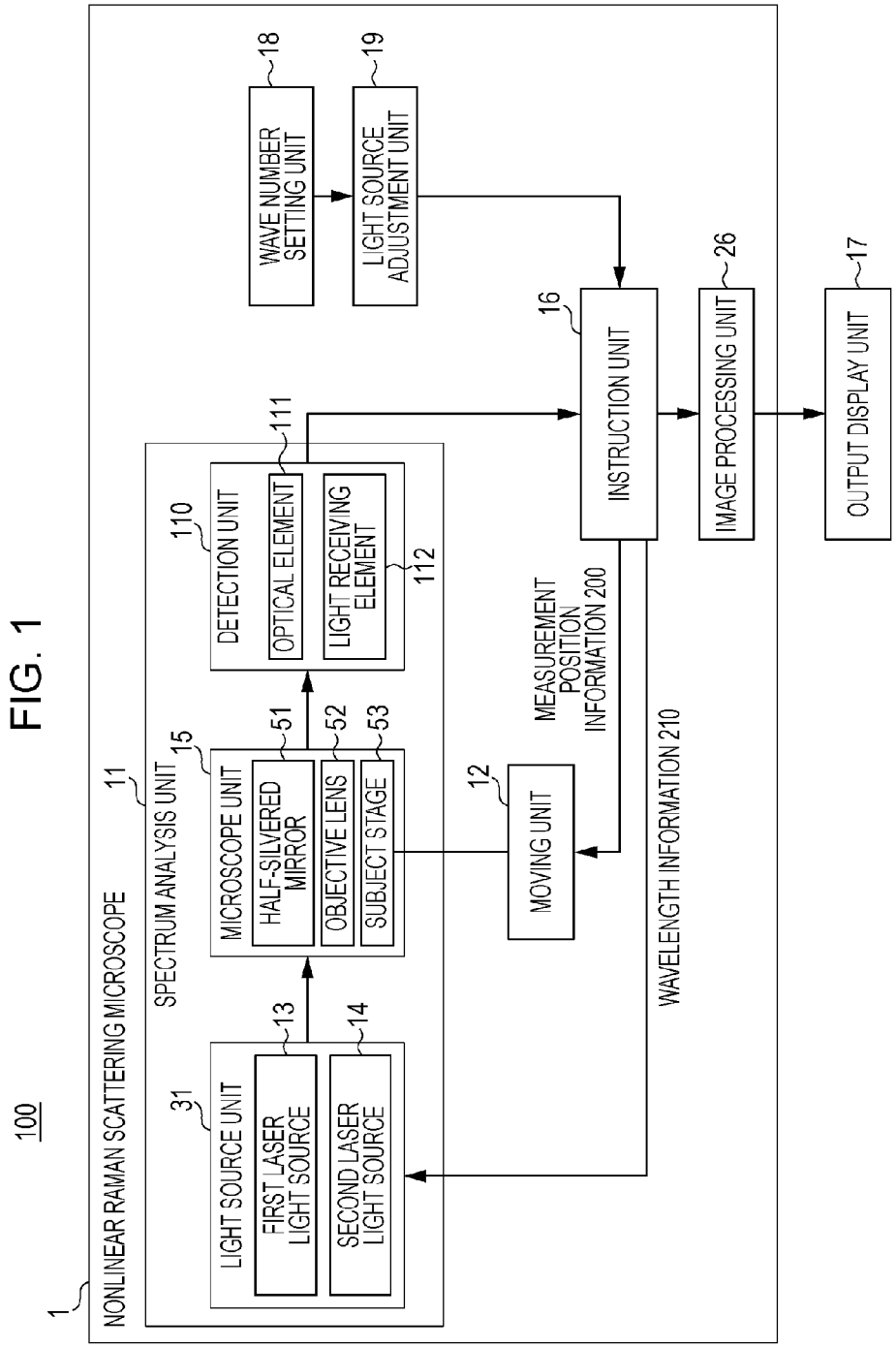
FIG. 1 is a block diagram illustrating a configuration of a subject information obtaining system according to a first exemplary embodiment.

In an optical measurement device in which a subject is irradiated with two focused laser beams having different wavelengths and light generated through nonlinear optical phenomena or the like is measured, it is necessary to set the wavelength of each of the laser beams in order to measure the subject at a desired measurement wave number. A combination of the wavelengths of two laser beams, however, is not uniquely determined from a measurement wave number, and thus an operator carrying out the measurement needs to perform a calculation as appropriate and to set the wavelength of each laser beam. Thus, it is cumbersome to adjust the measurement wave number. First through sixth exemplary embodiments described hereinafter provide an optical measurement device in which the measurement wave number can be adjusted more easily than in an existing technique.

In a nonlinear Raman scattering optical measurement device that utilizes coherent stimulated Raman scattering, coherent anti-Stokes Raman scattering, or the like, a subject is irradiated with two focused laser beams having different wavelengths (a first wavelength $\lambda 1$ and a second wavelength $\lambda 2$) and a molecular vibration is then measured. Thus, such an optical measurement device includes a first laser light source that emits a laser beam having the first wavelength $\lambda 1$ and a second laser light source that emits a laser beam having the second wavelength $\lambda 2$. In the present invention and in the present specification, a wave number that corresponds to the first wavelength $\lambda 1$ is referred to as a first wave number k1 ($k1 = 1/\lambda 1$), and a wave number that corresponds to the second wavelength $\lambda 2$ is referred to as a second wave number k2 ($k2 = 1/\lambda 2$). When measuring the subject with the nonlinear Raman scattering optical measurement device, a measurement wave number, which is a difference between the first wave number and the second wave number, is varied, and light from the subject obtained at a plurality of measurement wave numbers is detected.

In a two-photon absorption optical measurement device or in a sum frequency generation optical measurement device, a subject is irradiated with two focused laser beams (first wavelength $\lambda 1$ and second wavelength $\lambda 2$), and light from the subject is measured. Thus, light generated within the subject or light scattered within the subject is measured. Therefore, such an optical measurement device includes a first laser light source that emits a laser beam having the first wavelength $\lambda 1$ and a second laser light source that emits a laser beam having the second wavelength $\lambda 2$. In the two-photon absorption optical measurement device or the sum frequency generation optical measurement device, a measurement wave number, which is a sum of the first wave number and the second wave number, is varied, and light from the subject obtained at a plurality of measurement wave numbers is detected.

Aside from the optical measurement devices described above, the present invention can be applied to any optical measurement device (e.g., stimulated parametric optical measurement device) that is configured to obtain information on a subject by irradiating the subject with two focused laser beams having different wavelengths. Furthermore, the present invention can also be applied to an optical measurement device that merely obtains information on a subject, such as information on a molecular vibration or information on scattered light, but does not obtain an image. An optical measurement device to be described in the first through sixth exemplary embodiments hereinafter includes a measurement wave number setting unit (hereinafter, also referred to as a wave number setting unit) and a light source adjustment unit. The light source adjustment unit adjusts at least one of the first and second wavelengths such that a difference between the first wave number and the second wave number or a sum of the first wave number and the second wave number matches a measurement wave number set through the wave number setting unit. Note that varying the wave number causes the wavelength to vary as well, and thus the wave number may be used to adjust the wavelength. The light source adjustment unit determines the first and second wavelengths in accordance with the set measurement wave number, and outputs information on the determined first wavelength to the first laser light source and information on the determined second wavelength to the second laser light source. Through this, the measurement wave number is adjusted. The light source adjustment unit may determine the first and second wavelengths by, for example, referring to a table that indicates a relationship among the measurement wave number, the first wavelength, and the second wavelength. Alternatively, the light source adjustment unit may determine the first and second wavelengths by calculating a combination of the first wavelength and the second wavelength, upon the wave number setting unit setting the measurement wave number. The first laser light source emits a laser beam having the first wavelength in accordance with the information on the first wavelength obtained from the light source adjustment unit. In a similar manner, the second laser light source emits a laser beam having the second wavelength in accordance with the information on the second wavelength obtained from the light source adjustment unit. The above configuration makes it possible to measure the subject by using the measurement wave number set through the wave number setting unit.

Hereinafter, more detailed descriptions will be given on the basis of the first through sixth exemplary embodiments. In the first through fourth exemplary embodiments, a nonlinear Raman scattering optical measurement device will be described as an example. A sum frequency generation optical measurement device will be described in the fifth exemplary embodiment, and a two-photon absorption optical measurement device will be described in the sixth exemplary embodiment.

Aside from the optical measurement devices to be described in the first through sixth exemplary embodiments, the present invention can be applied to any optical measurement device that is configured to obtain information on a subject by irradiating the subject with two focused laser beams having different wavelengths. For example, the present invention can also be applied to an optical measurement device that merely obtains information on a molecular vibration but does not obtain an image.

Furthermore, the optical measurement devices described in the first through sixth exemplary embodiments typically adjust the measurement wave number multiple times while measuring a subject. In this manner, more advantageous effects of the present invention can be obtained when the present invention is applied to an optical measurement device that adjusts the measurement wave number multiple times.

First Exemplary Embodiment

FIG. 1 is a block diagram illustrating a configuration of a subject information obtaining system 100 according to the first exemplary embodiment. The subject information obtaining system of the first exemplary embodiment includes an optical measurement device and an output display unit 17. In the first exemplary embodiment, an optical microscope that utilizes nonlinear Raman scattering (hereinafter, referred to as a nonlinear Raman scattering microscope) serves as the optical measurement device. The nonlinear Raman scattering microscope 1 includes a spectrum analysis unit 11, a moving unit 12, an instruction unit 16, an image processing unit 26, a wave number setting unit 18, and a light source adjustment unit 19. The spectrum analysis unit 11 includes a light source unit 31 that includes a first laser light source 13 and a second laser light source 14, a microscope unit 15, and a detection unit 110. The configuration and structure of each unit will be described.

The light source unit 31 includes the first laser light source 13 and the second laser light source 14.

At least one of the first laser light source 13 and the second laser light source 14 is a laser light source of which the wavelength can be varied or selected and that emits a laser beam having a wavelength defined in wavelength information from the light source adjustment unit 19. In a case in which the first or second laser light source 13 or 14 is a laser light source of which the wavelength cannot be varied or selected and that emits a laser beam at a specific wavelength (hereinafter, referred to as a fixed wavelength light source), the light source adjustment unit 19 does not need to output wavelength information of a laser beam to be emitted from the fixed wavelength light source.

Although FIG. 1 illustrates a configuration in which the light source adjustment unit 19 outputs the wavelength information to at least one of the first and second laser light sources 13 and 14 through the instruction unit 16, a different configuration may be employed as long as that configuration allows the wavelength of a laser beam to be adjusted. For example, the light source adjustment unit 19 may output the wavelength information directly to the first and second laser light sources 13 and 14 without involving the instruction unit 16, or the instruction unit 16 may include the light source adjustment unit 19. The light source adjustment unit 19 can be formed by a computer that includes a calculation unit and a storage unit. The microscope unit 15 includes a half-silvered mirror 51, an objective lens 52, and a subject stage 53. The half-silvered mirror 51 converges the laser beam having the first wavelength and the laser beam having the second wavelength, and the subject placed on the subject stage 53 is irradiated with the laser beams through the objective lens 52. Note that the above-described configuration of the microscope unit 15 is merely an example, and the microscope unit 15 may have a different configuration.

The detection unit 110 includes an optical element 111 and a light receiving element 112 for extracting, from the light from the subject, light having a specific wavelength. The detection unit 110 detects an intensity of the light having the specific wavelength contained in the light from the subject and outputs the result of the detection to a computer. A filter, for example, can be used as the optical element 111.

The moving unit 12, which is connected to the subject stage 53 of the microscope unit 15, moves the sample stage 53 in response to receiving measurement position information from the instruction unit 16 to thus move the subject. Through this, the position of the subject relative to that of an irradiation area of the laser beams changes. Changing the position of the subject relative to that of the laser beam irradiation area as necessary makes it possible to scan the subject. An actuator, for example, can be used as the moving unit 12. Instead of moving the subject stage 53, the irradiation area of the laser beams may be moved so as to scan the subject. In this case, the moving unit 12, which is connected to the light source unit 31, moves the irradiation area of the laser beams in response to receiving measurement position information from the instruction unit 16. Depending on a range to be scanned, the focal positions of the laser beams may be moved by, for example, vibrating the half-silvered mirror 51 so as to change the position of the irradiation area relative to that of the subject, and the subject can thus be scanned.

Upon accepting input of information on measurement conditions under which the nonlinear Raman scattering microscope 1 measures the subject, the instruction unit 16 outputs information necessary to achieve the measurement conditions to each of the relevant units. Specifically, the instruction unit 16 outputs measurement position information to the moving unit 12 and outputs wavelength information 210 received from the light source adjustment unit 19 to the first and second laser light sources 13 and 14. The measurement position information may be inputted from a measurement position setting unit (not illustrated) or may be loaded from a storage unit connected to the instruction unit 16. The instruction unit 16 can be formed by a computer that includes a calculation unit and a storage unit.

The image processing unit 26 generates spectral data by integrating an optical intensity detected by the detection unit 10, a measurement position held when the optical intensity has been detected, and the measurement wave number. The generated spectral data contains information on the optical intensity (of light from the subject) that is dependent on the measurement position and the measurement wave number. The image processing unit 26 generates information on a spatial distribution of the optical spectrum, or in other words, information on the optical spectral image from the generated spectral data. The generated optical spectral image information is outputted to the output display unit 17. The image processing unit 26 can also be formed by a computer that includes a calculation unit and a storage unit. The instruction unit 16 and the image processing unit 26 may be installed in a single computer, or the instruction unit 16, the light source adjustment unit 19, and the image processing unit 26 may be installed in a single computer.

The output display unit 17 displays an image on the basis of the optical spectral image information outputted from the image processing unit 26. The output display unit 17 can be formed by any device that is capable of displaying an image and may, for example, be formed by a flat panel display or a printer. The output display unit 17 may include both a display and a printer. In addition, the output display unit 17 may display additional information on the optical spectral image, such as the measurement conditions.

Figure 2A:
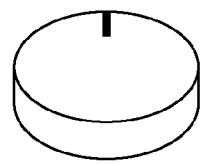
FIGS. 2A through 2D illustrate exemplary configurations of a measurement wave number setting unit.
Figure 2B:
Figure 2C:
Figure 2D:
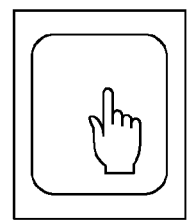

The wave number setting unit 18 allows the operator to set the measurement wave number. FIGS. 2A through 2D illustrate examples of the wave number setting unit 18 of the first exemplary embodiment, but the configuration of the wave number setting unit 18 is not particularly limited as long as a given configuration allows the operator to set the measurement wave number. FIG. 2A illustrates a dial, and the operator rotates the dial to set the measurement wave number. FIG. 2B illustrates a slider control, and the operator slides the control to set the measurement wave number. FIG. 2C illustrates a trackball, and the operator rotates the trackball in an X direction or a Y direction to set the measurement wave number. FIG. 2D illustrates a touch panel with a graphic user interface (GUI), and the operator drags in an X direction or a Y direction to set the measurement wave number. Alternatively, in place of providing a dedicated device, the wave number setting unit 18 may be displayed on the screen of the output display unit 17, and the operator may then set the measurement wave number by using a mouse or a keyboard. As another alternative, the configuration may be such that functions are switched as appropriate so as to allow the operator to set the measurement wave number by using a common operation device, such as a mouse. As yet another alternative, the nonlinear Raman scattering microscope 1 may include a plurality of wave number setting units, and the operator may select as appropriate a wave number setting unit to use among the plurality of wave number setting units.

While the operation amount of the wave number setting unit 18 and the measurement wave number may be in a continuous relationship or in a stepwise relationship, providing a linear relationship between the operation amount and the measurement wave number makes it possible to set the measurement wave number intuitively. Changing the speed at which the measurement wave number increases or decreases in accordance with the speed at which the wave number setting unit 18 is adjusted (e.g., the rotation speed in the case of the dial, or the sliding speed in the case of the slider control) makes it possible to set the measurement wave number quickly. Here, a separate unit for switching the speed at which the measurement wave number increases or decrease can be provided. As the operable range of the wave number setting unit 18 is greater, the measurement wave number can be set more precisely and in a broader range. When the measurement wave number is to be set through the wave number setting unit 18, displaying, in real time in the output display unit 17, spectral data obtained by measuring the wave number at the set measurement wave number or an image that is based on the obtained spectral data makes it possible to set the wave number more intuitively, more easily, or more strictly.

Upon accepting input of information on the measurement wave number set through the wave number setting unit 18, the light source adjustment unit 19 determines a combination of the first and second wavelengths that can achieve the set measurement wave number. The light source adjustment unit 19 then outputs the wavelength information to the first and second laser light sources 13 and 14 so that the first laser light source 13 emits a laser beam having the first wavelength and the second laser light source 14 emits a laser beam having the second wavelength. The first and second laser light sources 13 and 14 emit the laser beams having the first wavelength and the second wavelength, respectively, in accordance with the wavelength information received from the light source adjustment unit 19. The light source adjustment unit 19 may be formed, for example, by a computer that includes a calculation unit and a storage unit, as long as such a computer is capable of determining the first and second wavelengths upon accepting input of the information on the measurement wave number, and outputting the wavelength information to the first and second laser light sources 13 and 14. The light source adjustment unit 19 and the instruction unit 16 may be installed in a single computer, or the instruction unit 16, the image processing unit 26, and the light source adjustment unit 19 may be installed in a single computer. Here, the light source adjustment unit 19 may receive the information on the measurement wave number set through the wave number setting unit 18 from the instruction unit 16. In that case, the configuration may be such that an input device (e.g., a dial, a mouse) serving as the wave number setting unit 18 is connected to a computer in which the instruction unit 16, the image processing unit 26, and the light source adjustment unit 19 are installed.

Here, a combination of the first and second wavelengths that can achieve the set measurement wave number refers to such a combination that a difference between the first wave number (reciprocal of the first wavelength) and the second wave number (reciprocal of the second wavelength) matches the set measurement wave number. A Raman optical spectrum is often expressed by the optical intensity relative to the measurement wave number. In measurement such as nonlinear Raman scattering spectroscopy that uses two laser beams having the first wavelength and the second wavelength, the measurement wave number is expressed by a difference between the reciprocal of the first wavelength and the reciprocal of the second wavelength. Therefore, a combination of the first and second wavelengths is not uniquely determined for a given measurement wave number, and a combination needs to be selected from multiple combinations. The light source adjustment unit 19 determines a combination among a large number of combinations of the first and second wavelengths that can achieve the measurement wave number set through the wave number setting unit 18. Although the light source adjustment unit 19 outputs the wavelength information to at least one of the first and second laser light sources 13 and 14 in the first exemplary embodiment, the light source adjustment unit 19 may output wave number information instead of the wavelength information. In other words, the light source adjustment unit 19 may specify a laser beam to be emitted from at least one of the first and second laser light sources 13 and 14 by using a wave number. In a case in which the light source adjustment unit 19 is configured to output wave number information, the light source adjustment unit 19 determines a combination from a large number of combinations of the first wave number and the second wave number that can achieve a given measurement wave number.

When the light source adjustment unit 19 is to determine a combination of the first and second wavelengths, the light source adjustment unit 19 may refer to a table indicating a relationship among the measurement wave number, the first wavelength, and the second wavelength so as to determine a combination of the first and second wavelengths. This configuration can be implemented by, for example, storing the table in a storage unit of a computer in which the light source adjustment unit 19 is installed and allowing the light source adjustment unit 19 to load and refer to the table as necessary. The light source adjustment unit 19 may use a single table or a plurality of tables. In a case in which a plurality of tables are used, tables for several adjustment patterns may be stored in advance in the storage unit, and the operator may select a table while taking the subject and the types of the first and second laser light sources 13 and 14 into consideration. In this case, the operator may directly select a table to use by using a table selection unit or may indirectly select a table to use by selecting a measurement mode. For example, when measuring an organism or a subject derived from an organism, upon the operator selecting a biometry mode, the light source adjustment unit 19 may select, from the plurality of tables, a table that is suitable for measuring an organism and a subject derived from an organism. Alternatively, allowing the operator to create a reference table makes it possible to adjust the wave number in accordance with a subject even when a new subject is to be measured. As another alternative, the stated patterns may be combined as appropriate to determine the first and second wavelengths. Once a table is selected, table selection information that contains information as to which table has been selected is inputted to the light source adjustment unit 19.

In a case in which a plurality of tables are used, the tables serve to adjust different patterns.

For example, a table for adjusting the measurement wave number by changing the second wavelength in a direction different from a direction in which the first wavelength changes is created to serve as a first table. In addition, another table for adjusting one of the first and second wavelengths, while the other one of the first and second wavelengths is being fixed, in accordance with the measurement wave number is created to serve as a second table. Furthermore, yet another table for adjusting the first and second wavelengths such that the first and second wavelengths each vary possibly within a predetermined range is created to serve as a third table. The first through third tables are then stored, in advance, in the storage unit, and the operator can select as appropriate a table to use as described above. Alternatively, a table on which a plurality of combinations of the first and second wavelengths that can achieve a single measurement wave number are indicated may be used. In a case of using such a table, if the light source adjustment unit 19 can retain the first and second wavelengths held when the measurement wave number has been set, the light source adjustment unit 19 can select a combination of the first and second wavelengths that can quickly achieve the set measurement wave number from the plurality of combinations. A combination of the wavelengths that can quickly achieve the set measurement wave number corresponds to a combination in which an amount of change of each of the wavelengths is small. In a case in which the speed at which the wavelength changes differs for each of the first laser light source 13 and the second laser light source 14, however, it is preferable to determine a combination of the first and second wavelengths while taking the speed at which the wavelength of each of the first and second laser light sources 13 and 14 changes into consideration. For example, if the wavelength of the first laser light source 13 changes at a faster speed than the wavelength of the second laser light source 14, it is preferable to adjust the first and second wavelengths such that an amount of change of the first wavelength is greater than an amount of change of the second wavelength.

Here, the light source adjustment unit 19 receives information on the wavelengths (i.e., first and second wavelengths) of the laser beams being emitted from the first and second laser light sources 13 and 14 and can thus find the wavelengths of the first and second laser light sources 13 and 14.

Alternatively, the light source adjustment unit 19 may determine the first and second wavelengths by calculating a combination of the first and second wavelengths using a mathematical formula, instead of by referring to a table. In a case in which the light source adjustment unit 19 calculates a combination of the first and second wavelengths, it is preferable that the light source adjustment unit 19 retain the first and second wavelengths that have not been adjusted, as in the case of using a table on which a plurality of combinations of the first and second wavelengths are indicated. Then, it is preferable that the light source adjustment unit 19 calculate a combination of the first and second wavelengths that can quickly achieve the set measurement wave number, while taking the first and second wavelengths that have not been adjusted into consideration.

Subsequently, the operation of the optical measurement device (nonlinear Raman scattering optical measurement device) 1 according to the first exemplary embodiment will be described. The instruction unit 16 outputs the measurement wave number information set through the wave number setting unit 18 to the light source adjustment unit 19 and outputs the measurement position information to the moving unit 12. Upon receiving the measurement wave number information, the light source adjustment unit 19 determines the first and second wavelengths and outputs the wavelength information to the first and second laser light sources 13 and 14. Upon receiving the wavelength information, the first and second laser light sources 13 and 14 may each modify, if necessary, the wavelength of the laser beam to be emitted and output the laser beams. Meanwhile, upon receiving the measurement position information from the instruction unit 16, the moving unit 12, which is connected to the subject stage 53 of the microscope unit 15, moves the subject stage 53. Thus, the subject is irradiated with the focused laser beams emitted from the first and second laser light sources 13 and 14.

The detection unit 110 detects light emitted from the subject and outputs the result of the detection (light receiving signal) to the image processing unit 26 through the instruction unit 16. The image processing unit 26 generates spectral data by integrating the measurement position information, the measurement wave number information, and the optical intensity detected by the detection unit 110 and stores information on the generated spectral data in the storage unit. In addition, the image processing unit 26 generates optical spectral image information from the generated spectral data and outputs the generated optical spectral image information to the output display unit 17. The output display unit 17 displays an optical spectral image on the basis of the inputted information. Here, in the case of stimulated Raman scattering, the detection unit 110 detects the intensity of a reflected beam or a transmitted beam of a laser beam having the first or second wavelength. Meanwhile, in the case of coherent anti-Stokes Raman scattering, the detection unit 110 detects the intensity of scattered light having a wavelength that is different from either of the first and second wavelengths.

Figure 3:
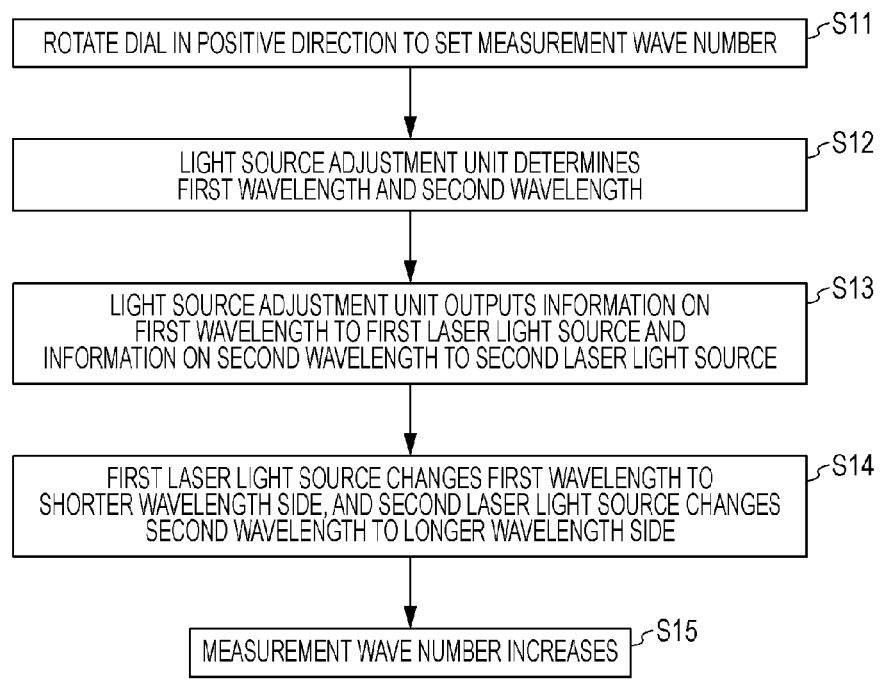
FIG. 3 is a flowchart illustrating processes for setting a measurement wave number and adjusting the measurement wave number.

An example in which the wave number is adjusted to a higher wave number in the first exemplary embodiment will be described with reference to a flowchart (see FIG. 3). Although an example in which the dial illustrated in FIG. 2A is used as the wave number setting unit 18 will be described hereinafter, even when a wave number setting unit other than the dial, such as a control, a trackball, a touch panel, a mouse, and a keyboard, is used, the wave number can be set in a manner similar to that of using the dial. When the measurement wave number is to be changed to a higher wave number, the dial is rotated in a positive direction so as to set the measurement wave number (S11). The light source adjustment unit 19 determines the first and second wavelengths in accordance with pre-established values stored in a table indicating the relationship among the measurement wave number and the first and second wavelengths (S12). For example, when the wave number setting unit 18 (e.g., any of FIGS. 2A to 2D) is acted upon, the light source adjustment unit 19 refers to the table (e.g., FIG. 4C) to determine the first and second wavelengths based on the angle of rotation. The light source adjustment unit 19 then outputs the determined first wavelength to the first laser light source 13 and the determined second wavelength to the second laser light source 14 (S13). In accordance with the inputted wavelength information (i.e., information on the first wavelength and information on the second wavelength), the first laser light source 13 shifts the first wavelength to a shorter wavelength side, and the second laser light source 14 shifts the second wavelength to a longer wavelength side (S14). Through this, the measurement wave number increases (S15), and the subject can be measured at the measurement wave number set through the wave number setting unit 18. In a case in which the measurement wave number changes in proportion to the change in the angle of rotation of the dial, the first and second wavelengths may change nonlinearly relative to the angle of rotation of the dial. If the range of the angle of rotation of the dial is set to 360° or greater, the measurement wave number can be set more precisely and in a broader range. Here, a plurality of dials may be provided, and assigning one dial to a coarse adjustment and another dial to a fine adjustment makes it possible to select the wave number precisely and quickly.

FIGS. 4A through 4C illustrate an example of a relationship among the angle of rotation of the dial, the measurement wave number, and the first and second wavelengths. FIG. 4A illustrates an angle of rotation θ of the dial; FIG. 4B is a graph schematically illustrating a relationship among the angle of rotation of the dial and the first and second wavelengths; and FIG. 4C illustrates a table indicating the relationship among the angle of rotation of the dial, the measurement wave number, and the first and second wavelengths. As illustrated in FIG. 4C, when the angle of rotation of the dial is 0°, the measurement wave number is 0 $cm^{-1}$. In this case, the first and second wavelengths are each 1125 nm. When the dial is rotated by 30°, the measurement wave number increases along with the rotation to 167 $cm^{-1}$. At this point, the light source adjustment unit 19 sets the first wavelength to 1115 nm and the second wavelength to 1135 nm in accordance with the table indicating the relationship among the measurement wave number and the first and second wavelengths. When the dial is further rotated and the angle of rotation of the dial is set to 180°, the measurement wave number becomes 1000 $cm^{-1}$, and the light source adjustment unit 19 sets the first wavelength to 1061 nm and the second wavelength to 1189 nm. While FIGS. 3, 4A, 4B, and 4C illustrate a case in which the second wavelength changes (or is swept) in a direction different from a direction in which the first wavelength changes upon the measurement wave number being changed, the manner in which the first and second wavelengths change is not limited to this example. For example, while the first wavelength is fixed, only the second wavelength may be changed so as to change the measurement wave number. Alternatively, the first and second wavelength may be changed in the same direction so as to change the measurement wave number.

The configuration in which the first wavelength and the second wavelength are swept in different directions as in the example illustrated in FIGS. 3, 4A, 4B, and 4C, however, enables faster wavelength sweeping than a configuration in which one of the first and second wavelengths is fixed and only the other one of the first and second wavelengths is swept or a configuration in which the first and second wavelengths are both swept in the same direction. Faster wavelength sweeping makes it possible to change the measurement wave number quickly. Therefore, when it is possible to change both the first and second wavelengths, it is preferable that the light source adjustment unit 19 change the second wavelength in a direction different from a direction in which the first wavelength changes. Here, that the second wavelength changes in a direction different from a direction in which the first wavelength changes means that the second wavelength decreases when the first wavelength increases or the second wavelength increases when the first wavelength decreases. The above, however, does not apply in a case in which there is a standard that takes higher priority over quickly changing the measurement wave number. Here, depending on the inputted measurement wave number, there may be a case in which the direction in which the first wavelength changes differs from the direction in which the second wavelength changes, or there may be a case in which the direction in which the first wavelength changes coincides with the direction in which the second wavelength changes.

In a case in which the wavelength of the first laser light source 13 changes at a faster speed than the wavelength of the second laser light source 14, it is preferable to determine the first wavelength and the second wavelength such that an amount of change of the first wavelength is greater than an amount of change of the second wavelength. Through this, even if a laser light source of which the wavelength changes at a slower speed and that is less expensive than the first laser light source 13 is used as the second laser light source 14, the time it takes to change the measurement wave number can be reduced.

Second Exemplary Embodiment

In the second exemplary embodiment, the method for adjusting the measurement wave number through the wave number setting unit 18 and the light source adjustment unit 19 of the first exemplary embodiment will be described in further detail with reference to FIGS. 5A to 5C.

As described above, there are a plurality of combinations of the first and second wavelengths that can achieve a given measurement wave number. In the second exemplary embodiment, a case in which the measurement wave number is adjusted quickly while laser light sources of the same type (i.e., the ranges of wavelengths at which the laser light sources can emit laser beams, least setting increments in which the wavelengths can be set, and the wavelength sweeping speeds are the same for the two laser light sources) are used as the first and second laser light sources will be described.

Figures 5A, 5B:
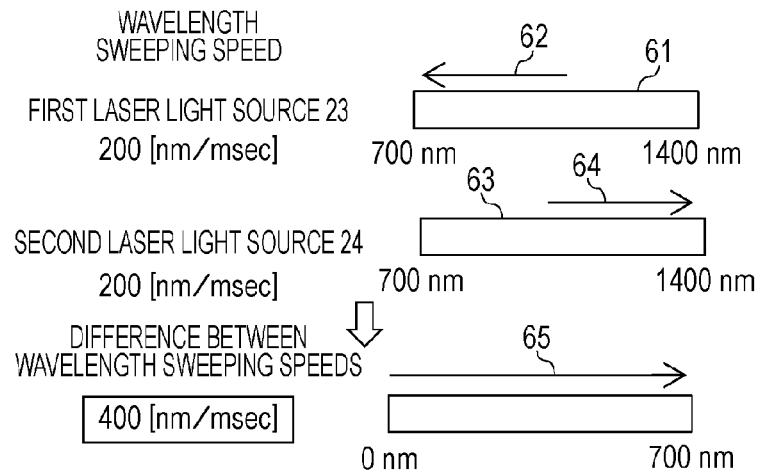
FIG. 5A schematically illustrates the first wavelength, the second wavelength, a difference between the wavelengths, and a speed of the change according to a second exemplary embodiment.
FIG. 5B is a table indicating a relationship among the angle of rotation of the dial, the measurement wave number, and the first and second wavelengths according to the second exemplary embodiment.

FIG. 5A schematically illustrates ranges 61 and 63 within which the wavelengths of first and second laser light sources 23 and 24 can be set, wavelength sweeping speeds 62 and 63, and a speed 65 at which the difference between the first wavelength and the second wavelength changes through wavelength sweeping. The first laser light source 23 and the second laser light source 24 are laser light sources of the same type, and the wavelength of a laser beam that can be emitted can be set continuously within a range from 700 nm to 1400 nm. In addition, the wavelength sweeping speeds 62 and 64 of the first and second laser light sources 23 and 24 are both 200 nm/msec. Here, the length of each arrow indicates the speed of wavelength sweeping, and a longer arrow indicates a greater speed.

FIG. 5B illustrates a relationship among the angle of rotation of the dial, the measurement wave number, and the first and second wavelengths according to the second exemplary embodiment. In the second exemplary embodiment, the first wavelength and the second wavelength are swept in different directions, and thus the measurement wave number can be changed quickly in one direction.

Figure 5C:
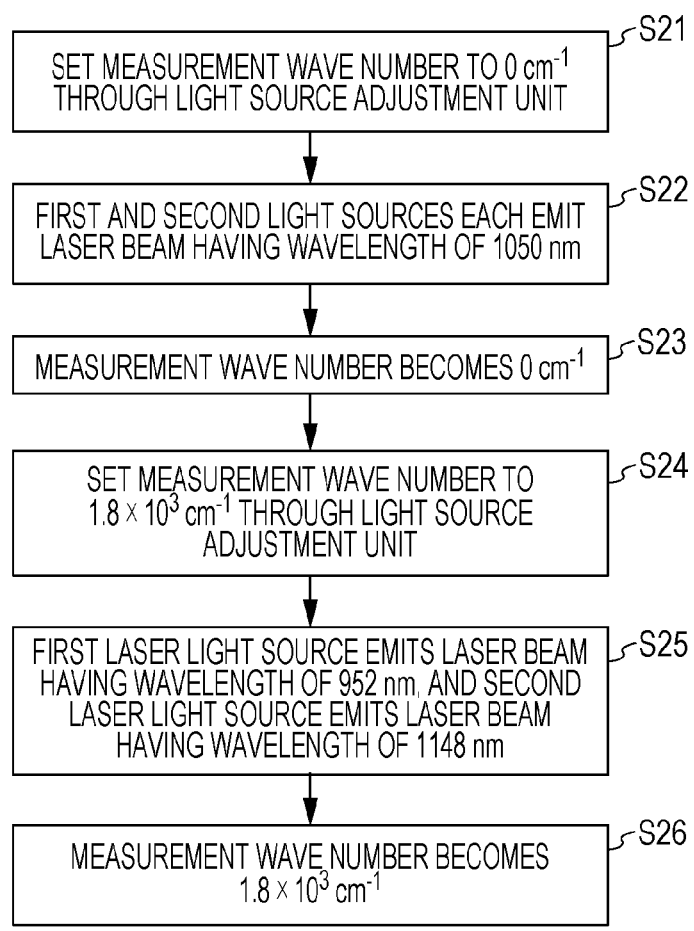
FIG. 5C illustrates a flow of processes for setting and adjusting the measurement wave number according to the second exemplary embodiment.

FIG. 5C illustrates a flow of processes for setting and adjusting the measurement wave number according to the second exemplary embodiment. In the second exemplary embodiment, the operator sets the measurement wave number to 0 $cm^{-1}$ by using the wave number setting unit 18 (S21). The first and second laser light sources 23 and 24 then each emit a laser beam having a wavelength of 1050 nm (S22), and the measurement wave number thus becomes 0 $cm^{-1}$ (S23). Thereafter, upon the operator setting the measurement wave number to $1.8 \times 10^3$ $cm^{-1}$ (S24), the first wavelength shifts to a shorter wavelength side, and the second wavelength shifts to a longer wavelength side. Thus, the first wavelength is set to 952 nm, and the second wavelength is set to 1148 nm. The first and second laser light sources 23 and 24 then emit laser beams at the set wavelengths (S25), and the measurement wave number in turn becomes $1.8 \times 10^3$ $cm^{-1}$ (S26). The speed at which the difference between the first and second wavelengths changes in this case is 400 nm/msec, which is the sum of the wavelength sweeping speeds of the first laser light source 23 and the second laser light source 24, and thus the measurement wave number can be changed more quickly in this case than in a configuration in which the wavelength of the laser beam from one of the first and second laser light sources 23 and 24 is fixed. Although a case in which the laser light sources of the same type are used as the first and second laser light sources 23 and 24 has been described in the second exemplary embodiment, a similar effect can be obtained even if laser light sources of different types are used, as long as the first wavelength and the second wavelength are changed in opposite directions along with an increase in the measurement wave number.

Third Exemplary Embodiment

In the third exemplary embodiment, the measurement wave number is adjusted through a method that is different from the method of the second exemplary embodiment, which will be described with reference to FIGS. 6A through 6C. In the third exemplary embodiment, a case in which the first laser light source and the second laser light source have different least setting increments in which the wavelengths of the first and second laser light sources can be set will be described.

Figures 6A, 6B:
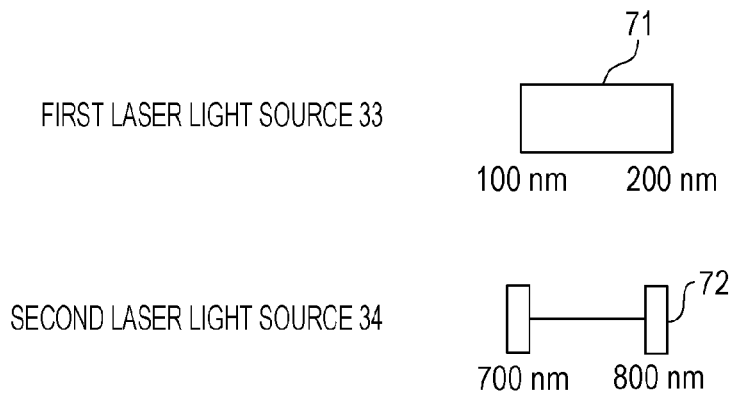
FIG. 6A schematically illustrates ranges within which the wavelengths of first and second laser light sources can be set according to a third exemplary embodiment.
FIG. 6B is a table indicating a relationship among the angle of rotation of the dial, the measurement wave number, and the first and second wavelengths according to the third exemplary embodiment.

FIG. 6A schematically illustrates ranges 71, 72 within which the wavelengths of first and second laser light sources 33 and 34 can be set. In the third exemplary embodiment, the first laser light source 33 is a laser light source of which the wavelength can be swept continuously in the range 71 from 100 nm to 200 nm. Meanwhile, the wavelength of the second laser light source 34 can be set only at two levels between 700 nm and 800 nm in increments of 100 nm. In other words, the first laser light source 33 has a least setting increment of 1 nm, and the second laser light source 34 has a least setting increment of 100 nm.

FIG. 6B illustrates a relationship among the angle of rotation of the dial, the measurement wave number, and the first and second wavelengths according to the third exemplary embodiment. In the third exemplary embodiment, when the set measurement wave number is small, the second wavelength is fixed at a shorter wavelength side (i.e., a side at which a difference from the first wavelength is smaller), and the measurement wave number is adjusted by changing only the first wavelength. Meanwhile, when the set measurement wave number is large, the second wavelength is fixed at a longer wavelength side (i.e., a side at which a difference from the first wavelength is larger), and the measurement wave number is adjusted by changing only the first wavelength.

Figure 6C:
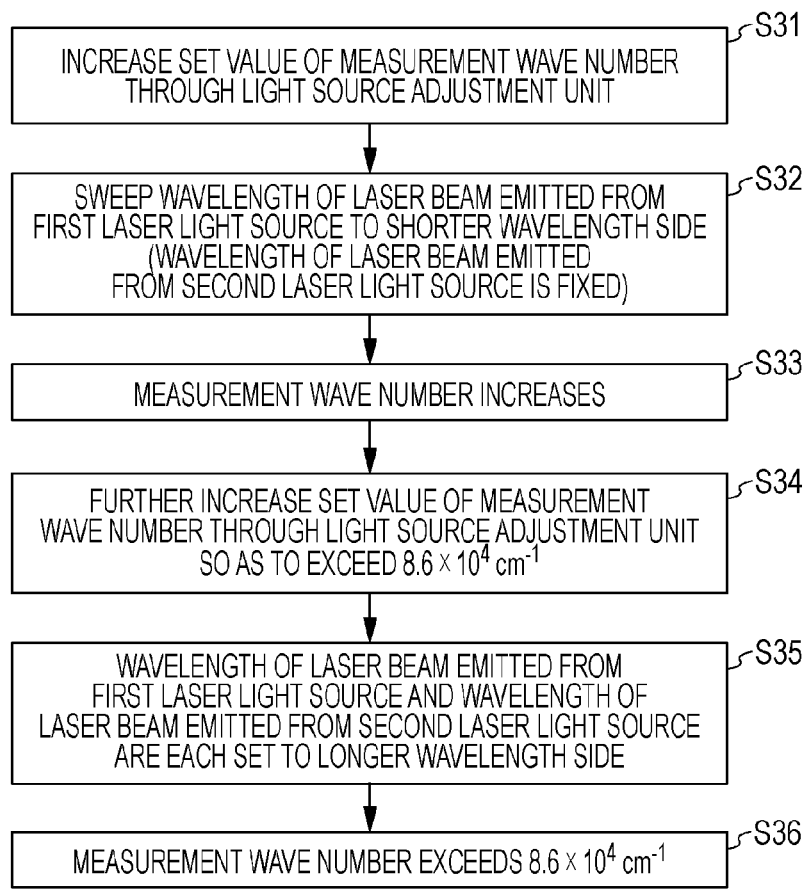
FIG. 6C illustrates a flow of processes for setting and adjusting the measurement wave number according to the third exemplary embodiment.

FIG. 6C illustrates a flow of processes for setting and adjusting the measurement wave number according to the third exemplary embodiment. The wave number is set in advance to a minimum value among the wave numbers that can be set through the wave number setting unit 18. The set value of the measurement wave number is increased through the wave number setting unit 18 (S31). When the set measurement wave number is small, the wavelength of the laser beam to be emitted from the second laser light source 34 is fixed at the shortest possible wavelength (700 nm). The wavelength of the laser beam emitted from the first laser light source 33 is then swept to a shorter wavelength side (S32), and thus the measurement wave number is adjusted in a positive direction (S33). Here, that the measurement wave number is small means that the set measurement wave number is smaller than the measurement wave number obtained when the first wavelength is set to the shortest possible wavelength (100 nm) of the first laser light source 33 and the second wavelength is set to the shortest possible wavelength (700 nm) of the second laser light source 34. When the second wavelength is fixed at 700 nm, the measurement wave number can vary within a range from $3.6 \times 10^4$ $cm^{-1}$ to $8.6 \times 10^4$ $cm^{-1}$. In this case, the second wavelength is fixed, and thus the first wavelength corresponding to the measurement wave number is uniquely determined.

When the measurement wave number is further changed in the positive direction, the set value of the measurement wave number exceeds $8.6 \times 10^4$ $cm^{-1}$ (S34). In that case, even if the first wavelength is set to the shortest possible wavelength, the set measurement wave number is unable to be achieved. Thus, the second wavelength is shifted to the longer wavelength side (800 nm) by 100 nm (by an amount of the least setting increment), and the first wavelength is shifted to a longer wavelength side (S35). Consequently, a measurement wave number that is greater than the measurement wave number obtained when the second wavelength is fixed at 700 nm (i.e., greater than $8.6 \times 10^4$ $cm^{-1}$) can be achieved (S36). When the second wavelength is fixed at 800 nm, the measurement wave number can vary within a range from $8.6 \times 10^4$ $cm^{-1}$ to $8.8 \times 10^4$ $cm^{-1}$. By adjusting the first and second wavelengths in this manner, the measurement wave number can be varied continuously in a range from $3.6 \times 10^4$ $cm^{-1}$ to $8.8 \times 10^4$ $cm^{-1}$.

In the second exemplary embodiment, as the set measurement wave number changes, the first and second wavelengths both change accordingly. Meanwhile, in the third exemplary embodiment, the second wavelength does not change while the measurement wave number varies within a range (e.g., $3.6 \times 10^4$ cm$^{-1}$ to $8.2 \times 10^4$ cm$^{-1}$) that is part of a range ($3.6 \times 10^4$ cm$^{-1}$ to $8.8 \times 10^4$ cm$^{-1}$) within which the measurement wave number can be set.

Fourth Exemplary Embodiment

In the fourth exemplary embodiment, the measurement wave number is adjusted through a method that is different from the methods of the second and third exemplary embodiments, which will be described with reference to FIGS. 7A to 7C. In the fourth exemplary embodiment, a case in which the subject is an organism or has derived from an organism will be described.

FIG. 7A schematically illustrates ranges 81, 82 within which the wavelengths of first and second laser light sources 43 and 44 can be set. In the fourth exemplary embodiment, the first laser light source 43 and the second laser light source 44 are of the same type and the wavelengths of the first laser light source 43 and the second laser light source 44 can be swept continuously in a range from 500 nm to 2000 nm.

When measuring a subject by using a nonlinear Raman scattering microscope, high-sensitive measurement can be achieved by using a laser wavelength in a band that is absorbed less by the subject. Typically, an organism absorbs less light in a wavelength range from 700 nm to 1400 nm inclusive and thus has high transmissivity in the stated range. Thus, in a case in which a subject of an organism or a subject derived from an organism is measured in a nonlinear Raman scattering microscope, it is preferable to set each of the first and second wavelengths within a range from 700 nm to 1400 nm inclusive.

In the fourth exemplary embodiment, in a case in which there is a combination of the first and second wavelengths that are each in a range from 700 nm to 1400 nm inclusive among combinations of the first and second wavelengths that can achieve the measurement wave number set though the wave number setting unit 18, the stated combination is selected by the light source adjustment unit 19. FIG. 7B illustrates combinations of the first and second wavelengths that, when the measurement wave number is set to $7.13 \times 10^3$ cm$^{-1}$, can achieve the set measurement wave number. As illustrated in FIG. 7B, there are a plurality of combinations of the first and second wavelengths that can achieve the measurement wave number of $7.13 \times 10^3$ cm$^{-1}$. The light source adjustment unit 19 of the fourth exemplary embodiment selects the second combination on the list in which the first and second wavelengths are both in a range from 700 nm to 1400 nm inclusive, and sets the first wavelength to 700 nm and the second wavelength to 1400 nm. In this manner, in the fourth exemplary embodiment, when the wave number set through the measurement wave number setting unit 18 is less than $7.13 \times 10^3$ cm$^{-1}$, the light source adjustment unit 19 selects such a combination in which the first and second wavelengths are both in a range from 700 nm to 1400 nm inclusive.

FIG. 7C illustrates a flow of processes for setting and adjusting the measurement wave number according to the fourth exemplary embodiment. Upon the operator setting the measurement wave number to $7.13 \times 10^3$ cm$^{-1}$ (S41), the light source adjustment unit 19 sets the first wavelength to 700 nm and the second wavelength to 1400 nm and outputs information on the first wavelength to the first laser light source 43 and information on the second wavelength to the second laser light source 44. Upon receiving the wavelength information, in accordance with the wavelength information, the first laser light source 43 emits a laser beam having a wavelength of 700 nm, and the second laser light source 44 emits a laser beam having a wavelength of 1400 nm (S42). Through this, the measurement wave number of $7.13 \times 10^3$ cm$^{-1}$ is achieved (S43).

In this manner, in the fourth exemplary embodiment, among the combinations of the wavelengths that can achieve the set measurement wave number, the light source adjustment unit 19 selects a combination that includes wavelengths having high transmittance through an organism. Therefore, when measuring a subject of an organism or a subject derived from an organism, the subject can be measured by using a combination of wavelengths that are suitable for that measurement. When a measurement wave number that cannot be achieved by a combination in which the first and second wavelengths are both in a range from 700 nm to 1400 nm inclusive is set, a wavelength that is shorter than 700 nm or a wavelength that is longer than 1400 nm is used as the first and second wavelengths. In this case, it is preferable to determine the first and second wavelengths such that as much amount of laser beams as possible passes through the subject. The stated range from 700 nm to 1400 nm inclusive can be modified as appropriate in accordance with the subject.

Thus far, the subject information obtaining system that includes the nonlinear Raman scattering microscope 1 as the optical measurement device has been described in the first through fourth exemplary embodiments. In the first through fourth exemplary embodiments, however, the optical measurement device is not limited to an optical measurement device that utilizes nonlinear Raman scattering or to a microscope, as long as the optical measurement device uses a difference between the first wave number and the second wave number as the measurement wave number. In addition, the first through fourth exemplary embodiments can also be applied to an optical measurement device that uses the sum of the first wave number and the second wave number as the measurement wave number. An exemplary embodiment of an optical measurement device that uses the sum of the first wave number and the second wave number as the measurement wave number will be described in detail.

Fifth Exemplary Embodiment

In the fifth exemplary embodiment, a sum frequency generation optical measurement device is used as the optical measurement device. Thus, the fifth exemplary embodiment differs from the first through fourth exemplary embodiments in that the sum of the first wave number and the second wave number serves as the measurement wave number. In addition, the fifth exemplary embodiment differs from the first through fourth exemplary embodiments in that the light source adjustment unit 19 specifies the laser beams to be emitted from the first and second laser light sources by using information on the wave number, but is substantially the same as the first through fourth exemplary embodiments in terms of the other configurations. Thus, detailed descriptions of the configurations that are similar to those of the first through fourth exemplary embodiments will be omitted.

The configuration of the sum frequency generation optical measurement device of the fifth exemplary embodiment is substantially the same as the configuration of the nonlinear Raman scattering microscope 1 illustrated in FIG. 1, and thus drawings and detailed descriptions thereof will be omitted.

Figures 8A, 8B:
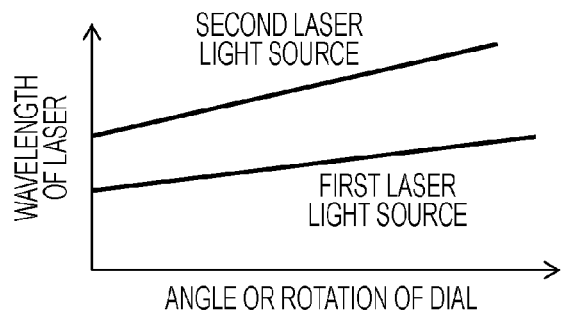
FIG. 8A is a graph schematically illustrating a relationship among the angle of rotation of the dial, the measurement wave number, and first and second wave numbers according to a fifth exemplary embodiment.
FIG. 8B is a table indicating a relationship among the angle of rotation of the dial, the measurement wave number, and the first and second wave numbers according to the fifth exemplary embodiment.
Figure 8C:
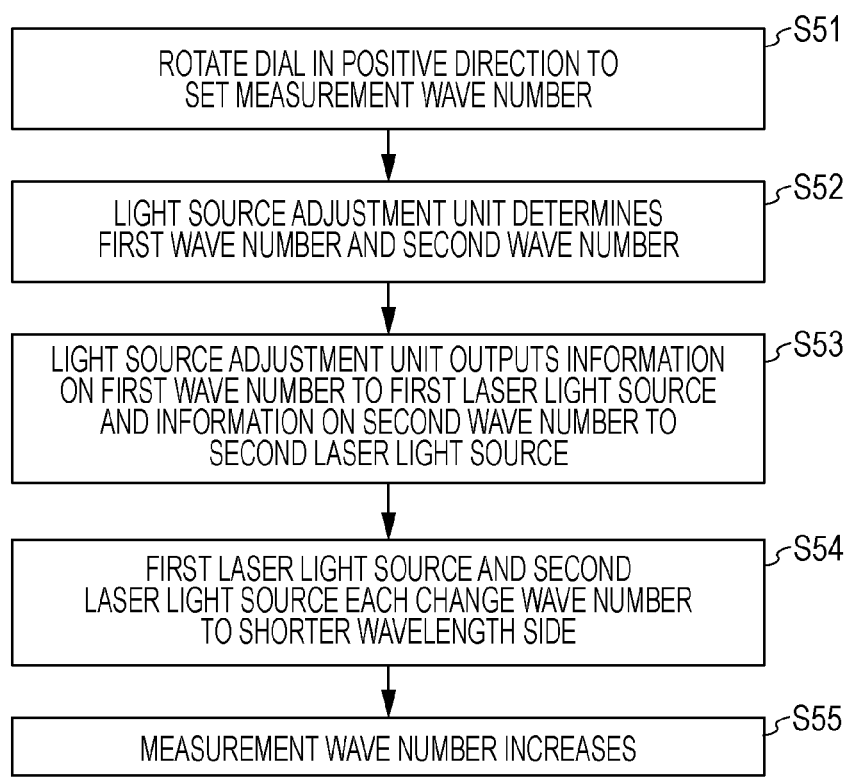
FIG. 8C illustrates a flow of processes for setting and adjusting the measurement wave number according to the fifth exemplary embodiment.

As in the nonlinear Raman scattering microscope 1, the angle of rotation of the dial serving as the wave number setting unit 18 is associated with the measurement wave number, and the operator can thus set the measurement wave number by using the dial. The light source adjustment unit 19 then adjusts the first wavelength and the second wavelength such that the set measurement wave number matches the sum of the first wave number and the second wave number. FIGS. 8A through 8C illustrate an example of a method for adjusting the first and second wavelengths by the light source adjustment unit 19.

An example of adjusting the wave number to a higher wave number in the fifth exemplary embodiment will be described with reference to a flowchart illustrated in FIG. 8C. Although an example in which the dial illustrated in FIG. 2A is used as the wave number setting unit 18 will be described here, a wave number setting unit aside from the dial can also be used as in the first through fourth exemplary embodiments. When the measurement wave number is changed to a higher wave number, the dial is rotated in a positive direction so as to set the measurement wave number. The light source adjustment unit 19 determines the first and second wavelengths in accordance with the table indicating the relationship among the measurement wave number and the first and second wavelengths. FIG. 8B illustrates an example of a table to be used by the light source adjustment unit 19. FIG. 8B illustrates a table that indicates a relationship among the angle of rotation of the dial, the measurement wave number, and the first and second wave numbers. FIG. 8A is a graph that schematically illustrates a relationship among the angle of rotation of the dial, the measurement wave number, and the first and second wave numbers.

For example, when the dial is rotated in a positive direction and the angle of rotation of the dial is set to 180°, the measurement wave number is set to $1.9 \times 10^3$ cm$^{-1}$ (S51). The light source adjustment unit 19 refers to the table and sets the first wave number to $8.0 \times 10^2$ cm$^{-1}$ and the second wave number to $1.1 \times 10^3$ cm$^{-1}$ (S52). The light source adjustment unit 19 then outputs information on the set first wave number to the first laser light source and information on the set second wave number to the second laser light source (S53). In accordance with the inputted wave number information, the first and second laser light sources each increase the wave number (i.e., shift the wavelength to a shorter wavelength side) of the laser beam to be emitted (S54). Through this, the measurement wave number increases (S55), and the subject can be measured at the measurement wave number set through the wave number setting unit 18. As in the first exemplary embodiment, in a case in which the measurement wave number changes in proportion to the change in the angle of rotation of the dial, the first and second wavelengths may change nonlinearly relative to the angle of rotation of the dial. If the range of the angle of rotation of the dial is set to 360° or greater, the measurement wave number can be set more precisely and in a broader range. Here, a plurality of dials may be provided, and assigning one dial to a coarse adjustment and another dial to a fine adjustment makes it possible to select the wave number precisely and quickly.

Although a case in which two lasers are used has been described in the fifth exemplary embodiment, the fifth exemplary embodiment can also be applied in a case in which three or more lasers are used or in a case in which the wavelength of a single laser is divided into a plurality of wavelengths and the wavelengths are then converted through a wavelength converter.

Sixth Exemplary Embodiment

In the sixth exemplary embodiment, a two-photon absorption measurement device is used as the optical measurement device. Thus, the sixth exemplary embodiment differs from the first through fourth exemplary embodiments in that the measurement wave number is the sum of the first wave number and the second wave number. The sixth exemplary embodiment, however, is substantially the same as the first through fourth exemplary embodiments in terms of other configurations. Thus, detailed descriptions of the configurations that are similar to those of the first through fourth exemplary embodiments will be omitted.

The wave number setting unit 18 and the light source adjustment unit 19 set the measurement wave number and adjust the measurement wave number by adjusting the first wave number and the second wave number in a similar manner to that in the fifth exemplary embodiment, and thus detailed descriptions thereof will be omitted.

A method for adjusting the measurement wave number in the sixth exemplary embodiment will be described with reference to FIGS. 9A and 9B. When measuring a subject by using a two-photon absorption measurement device, high-sensitive measurement can be achieved by using a laser wavelength in a band that is absorbed less by the subject at a portion other than a target portion. Described as an example is a case in which a subject of which the measurement wave number for exciting a target portion within the subject is $2.86 \times 10^4$ cm$^{-1}$ and a single-photon absorption wave number of a substance other than the target portion (i.e., impurity) within the subject is $1.43 \times 10^4$ cm$^{-1}$ is measured.

Figure 9B:
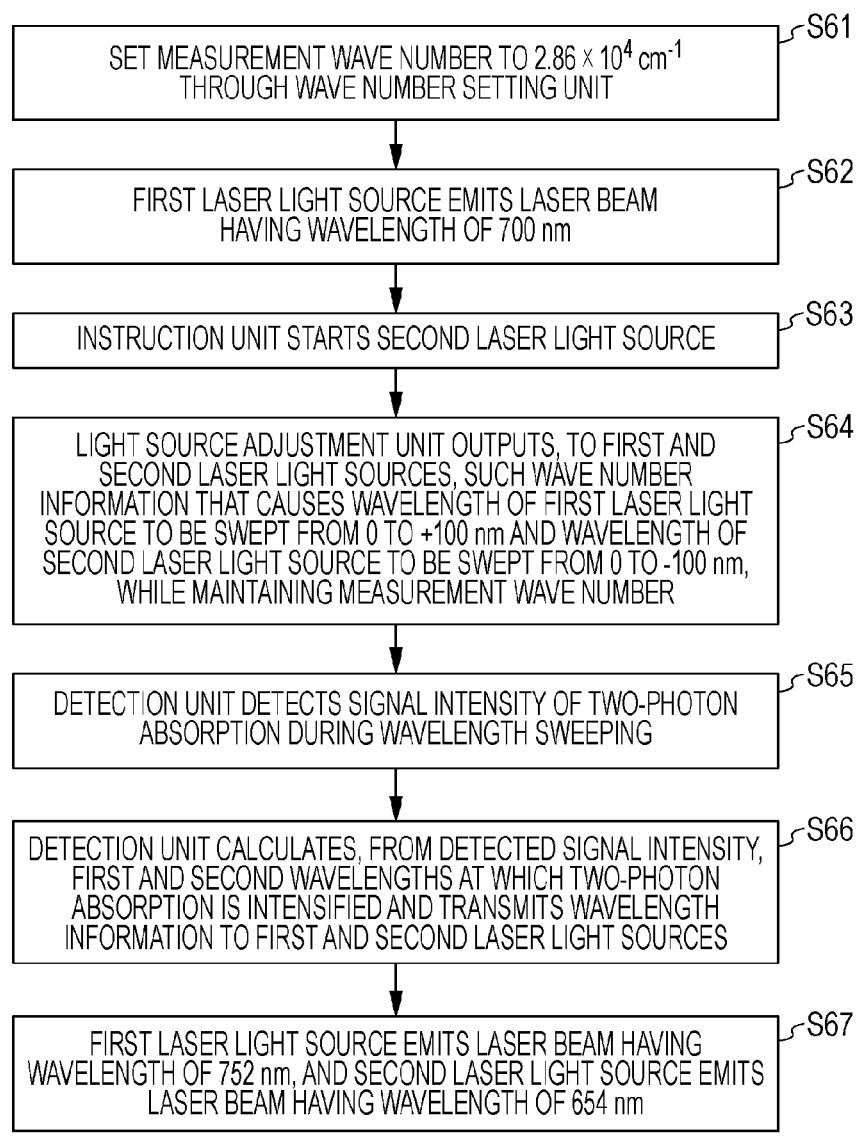
FIG. 9B illustrates a flow of processes for setting and adjusting the measurement wave number according to a sixth exemplary embodiment.

FIG. 9B illustrates a flowchart of processes for setting and adjusting the measurement wave number according to the sixth exemplary embodiment. Although the measurement starts in a mode in which only one of the laser light sources is used in the sixth exemplary embodiment, the measurement may start in a mode in which the two laser light sources are used. Upon the operator setting the measurement wave number to $2.86 \times 10^4$ cm$^{-1}$ (S61), the light source adjustment unit 19 sets the first wavelength to 700 nm. Since the measurement starts in a mode in which the second laser light source is not used, the first wavelength is uniquely determined upon the measurement wave number being set. The light source adjustment unit 19 outputs information on the first wavelength to the first laser light source. Upon receiving the wavelength information, the first laser light source emits a laser beam having a wavelength of 700 nm in accordance with the wavelength information (S62). Through this, the measurement wave number of $2.86 \times 10^4$ cm$^{-1}$ is achieved.

The subject to be measured in the sixth exemplary embodiment, however, contains an impurity that exhibits single-photon absorption at a wavelength of 700 nm, and thus the use of a laser beam at a wavelength of 700 nm makes it difficult to measure the subject with high sensitivity. The instruction unit 16 detects that the subject contains an impurity that exhibits single-photon absorption at a wavelength of the laser beam being used for the measurement on the basis of a result of detection by the detection unit and starts the second laser light source (S63). Through this, a mode in which the two laser light sources are used starts.

In the sixth exemplary embodiment, the light source adjustment unit 19 outputs, to the first laser light source and the second laser light source, such wavelength information that causes the wavelength of the first laser light source to be swept from 0 to +100 nm and the wavelength of the second laser light source to be swept from 0 to −100 nm, while the measurement wave number is maintained (S64). Upon receiving the wavelength information, in accordance with the wavelength information, the first laser light source emits a laser beam having a wavelength in a range from 700 to 800 nm, and the second laser light source emits a laser beam having a wavelength in a range from 700 to 600 nm. During wavelength sweeping, the detection unit 110 detects a signal intensity of two-photon absorption of the target portion for each wavelength and transmits the result to the instruction unit 16. The signal intensity information is recorded by the instruction unit 16 or the image processing unit 26 (S65).

The instruction unit 16 or the image processing unit 26 calculates, from the recorded signal intensity information, the first and second wavelengths at which the target portion exhibits a high two-photon absorption signal intensity and outputs the calculated wavelength information to the first and second laser light sources (S66). Upon receiving the wavelength information, in accordance with the wavelength information, the first laser light source emits a laser beam having a wavelength of 752 nm, and the second laser light source emits a laser beam having a wavelength of 654 nm (S67). In the table illustrated in FIG. 9A, the upper row indicates the measurement wave number, the first and second wave numbers, and the first and second wavelengths held in a mode in which only one of the laser light sources is used. Meanwhile, in the table illustrated in FIG. 9A, the lower row indicates the first and second wavelengths calculated from the signal intensity during wavelength sweeping and the measurement wave number and the first and second wave numbers that correspond to the calculated first and second wavelengths.

Although the wavelength that is absorbed by the impurity contained in the subject may be detected at the time of the measurement as described above, the subject may be measured in advance with single-photon absorption and an absorption wavelength of the impurity obtained through the measurement may be stored in the instruction unit. Through this, the second laser light source can be started when the measurement wave number corresponding to the obtained absorption wavelength has been set, and thus the measurement at the set measurement wave number can be carried out promptly. Alternatively, the first and second laser light sources may both be started at the beginning, and the first and second wavelengths at which a target two-photon absorption signal intensity increases may be identified by sweeping the wavelengths of the first and second laser light sources.

Although the wavelength sweeping range is not limited to ±100 nm, a laser beam having a short wavelength is less likely to reach a deep portion within a subject, and thus it is preferable that the operator set the wavelength sweeping range in accordance with the type of the subject. In addition, using a laser beam has a wavelength that is as long as possible is advantageous in observing a deep portion within a subject, and thus the wavelengths of the first and second wavelengths may be set to the same wavelength. It is necessary to sweep the wavelengths of the first laser light source and the second laser light source in opposite directions. Although wavelength selection processing of the laser light sources can be carried out at each measurement point in a case in which a subject is not a homogeneous substance, it is preferable, in terms of the measurement time, to assign a plurality of measurement points for a single instance of the aforementioned processing. Although a laser light source that is not capable of continuous wavelength sweeping can also be used in the sixth exemplary embodiment, the measurement wave number needs to be held constant during the wavelength sweeping, and thus at least one of the laser light sources needs to be capable of continuous wavelength sweeping. The sixth exemplary embodiment can also be applied to a multiphoton absorption measurement device, such as a three or more photon absorption measurement device, if the angle of rotation of the dial, the measurement wave number, and the wave numbers of the two laser light sources are associated with one another in advance.

While the first through sixth exemplary embodiments have been described thus far, in each of the exemplary embodiments, the first and second laser light sources may each be formed by a plurality of laser light sources having different variable wavelength bands. As one exemplary configuration, a plurality of laser light sources having different wavelength bands may be combined into a single laser light source so as to operate as the first or second laser light source. Alternatively, as another exemplary configuration, two laser light sources may be selected from three or more laser light sources having different variable wavelength bands; then, one of the selected laser light sources may be used as the first laser light source, and the other one of the selected laser light sources may be used as the second laser light source. The latter configuration can reduce the number light sources. In this manner, if the first or the second laser light source is formed by a plurality of laser light sources, a single laser light source that is capable of emitting a laser beam at a wavelength specified through the wave number setting unit 18 is to be selected from the plurality of laser light sources when adjusting the wavelengths of the first and second laser light sources. Here, a table that indicates which light source is to be selected in accordance with the set measurement wave number may be provided in advance, and a laser light source may be selected automatically by referring to that table. Alternatively, the operator may select a laser light source through a light source selection unit, such as a control and a dial. After a laser light source is selected, the selected laser light source is configured to emit a laser beam at a specified wavelength. The above configuration makes it possible to substantially broaden the variable wavelength band, and thus the measurement wave number range can be broadened.

Other Embodiments

An exemplary embodiment of the present invention can also be realized by carrying out the following processing. Specifically, software (wavelength adjustment program) that realizes each step in the method for determining the first and second wavelengths implemented by the light source adjustment unit 19 in the exemplary embodiments described above is supplied to a calculation unit, and a computer (or a CPU, an MPU, or the like) loads and executes the program. The program can be supplied to the calculation unit through a network or in the form of various types of storage media. Note that the method for determining the first and second wavelengths includes the following steps. In the first step, at least one of the first and second wavelengths is determined such that a difference between the first wave number and the second wave number matches a measurement wave number included in inputted information on the measurement wave number (i.e., measurement wave number set through the wave number setting unit). In the second step, the information determined in the first step is outputted.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-115682 filed May 31, 2013 and Japanese Patent Application No. 2014-069415 filed Mar. 28, 2014, which are hereby incorporated by reference herein in their entirety.

What is claimed is:

1. An optical measurement device, comprising:
a light source unit including a first laser light source and a second laser light source, the first laser light source being configured to emit a laser beam having a first wavelength, the second laser light source being configured to emit a laser beam having a second wavelength;
a measurement wave number setting unit; and
a light source adjustment unit configured to adjust at least one of the first wavelength and the second wavelength such that a difference between or a sum of a first wave number corresponding to the first wavelength and a second wave number corresponding to the second wavelength matches a measurement wave number set through the measurement wave number setting unit.

2. The optical measurement device according to claim 1, wherein the light source adjustment unit is capable of adjusting the first wavelength and the second wavelength.

3. The optical measurement device according to claim 2, wherein the second wavelength changes in a direction different from a direction in which the first wavelength changes, upon the measurement wave number set through the measurement wave number setting unit being changed.

4. The optical measurement device according to claim 2, wherein a least setting increment of the first wavelength of the first laser light source is less than a least setting increment of the second wavelength of the second laser light source, and
wherein the light source adjustment unit adjusts the first wavelength but does not adjust the second wavelength in a case in which the measurement wave number varies within part of a range of measurement wave numbers that can be set through the measurement wave number setting unit.

5. The optical measurement device according to claim 2, wherein the first wavelength of the first laser light source changes at a faster speed than the second wavelength of the second laser light source, and
wherein the light source adjustment unit adjusts the first wavelength and the second wavelength such that an amount of change in the first wavelength is greater than an amount of change in the second wavelength.

6. The optical measurement device according to claim 1, wherein the light source adjustment unit adjusts at least one of the first wavelength and the second wavelength such that the first wavelength and the second wavelength fall within a range from 700 nm to 1400 nm inclusive, in a case in which the measurement wave number set through the measurement wave number setting unit is less than $7.13 \times 10^3$ cm$^{-1}$.

7. The optical measurement device according to claim 1, wherein the light source adjustment unit determines the first wavelength and the second wavelength by referring to a table that indicates a relationship among the measurement wave number, the first wavelength, and the second wavelength.

8. The optical measurement device according to claim 7, wherein the light source adjustment unit selects a table from a plurality of tables each indicating a relationship among the measurement wave number, the first wavelength, and the second wavelength and determines the first wavelength and the second wavelength by referring to the selected table.

9. The optical measurement device according to claim 8, wherein the light source adjustment unit selects a table to refer to in accordance with table selection information inputted from a table selection unit.

10. The optical measurement device according to claim 1, wherein the light source adjustment unit determines the first wavelength and the second wavelength by calculating a combination of the first wavelength and the second wavelength in which a difference between of the first wave number and the second wave number matches a wave number set through the measurement wave number setting unit.

11. The optical measurement device according to claim 1, wherein the measurement wave number setting unit includes at least one device among a dial, a control, a trackball, a touch panel, a mouse, and a keyboard.

12. The optical measurement device according to claim 1, wherein the measurement wave number setting unit is capable of setting the measurement wave number continuously or stepwise in accordance with an operation amount.

13. The optical measurement device according to claim 1, wherein the measurement wave number setting unit displays the set measurement wave number to an operator.

14. The optical measurement device according to claim 1, wherein the light source adjustment unit displays the first wavelength and the second wavelength to an operator.

15. The optical measurement device according to claim 1, wherein the optical measurement device is a two-photon absorption measurement device, and
wherein the optical measurement device includes a function for selecting between a first mode in which a subject is not irradiated with the laser beam from the second laser light source and a second mode in which the subject is irradiated with the laser beams from the first laser light source and the second laser light source.

16. An optical microscope, comprising:
the optical measurement device according to claim 1;
a detection unit configured to detect at least part of light emitted from a subject, the light being emitted in response to the subject being irradiated with the laser beams from the light source unit; and
an image processing unit configured to generate spectral data on the basis of a result of detection by the detection unit and to generate image information from the spectral data.

17. The optical microscope according to claim 16, wherein the detection unit detects fluorescent light or Raman scattered light emitted from the subject in response to the subject being irradiated with the laser beams.

18. A subject information obtaining system, comprising:
the optical microscope according to claim 16; and
an output display configured to display an image that is based on the image information outputted from the image processing unit.

19. A light source adjustment unit configured to adjust one of a first wavelength and a second wavelength by outputting wavelength information to at least one of a first laser light source that emits a laser beam having a first wavelength and a second laser light source that emits a laser beam having a second wavelength,
wherein the light source adjustment unit is configured to adjust at least one of the first wavelength and the second wavelength such that a difference between of a first wave number corresponding to the first wavelength and a second wave number corresponding to the second wavelength matches a measurement wave number set through a measurement wave number setting unit.

20. A computer-readable storage medium storing a program for causing a computer to perform a wavelength adjustment process, comprising:

determining at least one of a first wavelength and a second wavelength such that a different between of a first wave number corresponding to the first wavelength and a second wave number corresponding to the second wavelength matches a measurement wave number included in inputted measurement wave number information; and outputting information determined in the determining of at least one of the first wavelength and the second wavelength.

* * * * *